United States Patent [19]

Hsu

[11] Patent Number: 5,800,212

[45] Date of Patent: Sep. 1, 1998

[54] PLUG-IN TYPE LIGHT BULB

[76] Inventor: Min-Hsun Hsu, 12F-1, No.311, Sec.4, Chung Hsiao E. Rd., Taipei, Taiwan

[21] Appl. No.: 807,279

[22] Filed: Feb. 28, 1997

[51] Int. Cl.$^6$ ..................................................... H01R 17/00
[52] U.S. Cl. ............................................................ 439/619
[58] Field of Search ...................................... 439/611, 612, 439/619, 699.2, 356, 375

[56] References Cited

U.S. PATENT DOCUMENTS 4,877,992  10/1989  Devir ..................................... 439/611

*Primary Examiner*—Gary F. Paumen
*Assistant Examiner*—Yong Ki Kim
*Attorney, Agent, or Firm*—Rosenberg, Klein & Bilker

[57] ABSTRACT

An improved plug-in type light bulb including a light bulb with a plug unit and an electrical socket for receiving the light bulb. The socket is comprised of two symmetrical halves each of which includes an upper portion and a lower portion. A cover plate with a notch is disposed inside at the upper portion, while a plurality of grooves are formed at the lower portion. A plurality of electrically conductive plates are disposed in the grooves and each of which has an angular contact terminal. The plug unit has two side walls each of which has an integrally formed raised block and two lateral walls against which the corresponding contact terminals of the lead wires rest. The lateral walls are further provided with a respective half round groove across which the contact terminal is disposed. When the light bulb is inserted into the socket, the angular contact terminals of the conductive plates will fit into the insert grooves of the plug unit of the light bulb and cause a part of the respective contact terminals of the lead wires to fit into the same insert grooves to achieve firm electrical contact.

1 Claim, 6 Drawing Sheets

PLUG-IN TYPE LIGHT BULB

BACKGROUND OF THE INVENTION (a) Field of the Invention

The present invention relates generally to a plug-in type light bulb, and more particularly to an improved plug-in type light bulb which requires a minimal number of electrically conductive plates and provides enhanced electrical contact.

(b) Description of the Prior Art

A prior plug-in type light bulb for use in cars is shown in FIG. 1. It essentially comprises a light bulb 1 and a plug unit 2 at its bottom, as well as an electrical socket 4 for connection with electricity. A couple of lead wires 3 of the light bulb 1 are configured to have their respective contact terminals 31 arranged to one end of the respective side walls 21. Hence, the corresponding grooves 43 of the two socket halves 42 of the socket 4 need to be provided with respective electrically conductive plates 5. It can be seen that at least four conductive plates 5 are needed to match the configuration of the plug unit 2. There are the following drawbacks with such a prior device:

1. At least four conductive plates 5 are needed, which is costly.
2. Contact between the conductive plates 5 and the contact terminals 31 of the lead wires 3 may not be good under vibration.

SUMMARY OF THE INVENTION

A primary object of the present invention is to provide a plug-in type light bulb with lead wires having their contact terminals provided at the lateral walls of a plug unit so as to reduce the number of the required electrical conductive plates by at least half and hence lower costs.

Another object of the present invention is to provide a light bulb in which there is a good and firm contact between the contact terminals of the lead wires of the light bulb and those of the electrically conductive plates of the electrical socket.

BRIEF DESCRIPTION OF THE DRAWINGS

The foregoing and other features and advantages of the present invention will be more clearly understood from the following detailed description and the accompanying drawings, in which.

DETAILED DESCRIPTION OF THE PREFERRED EMBODIMENT

Figure 1:
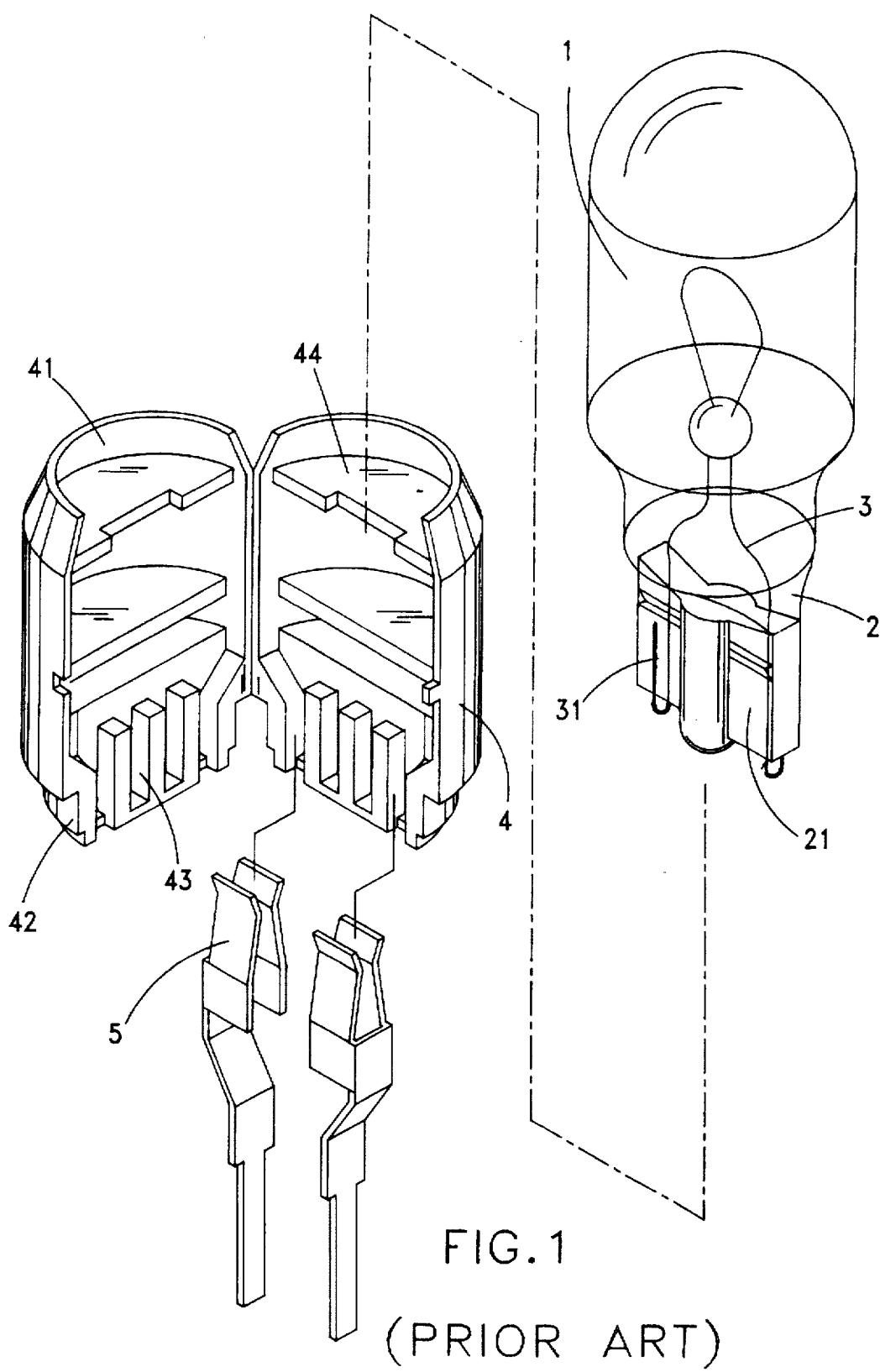
FIG. 1 is a schematic exploded view of the prior art.
Figure 2:
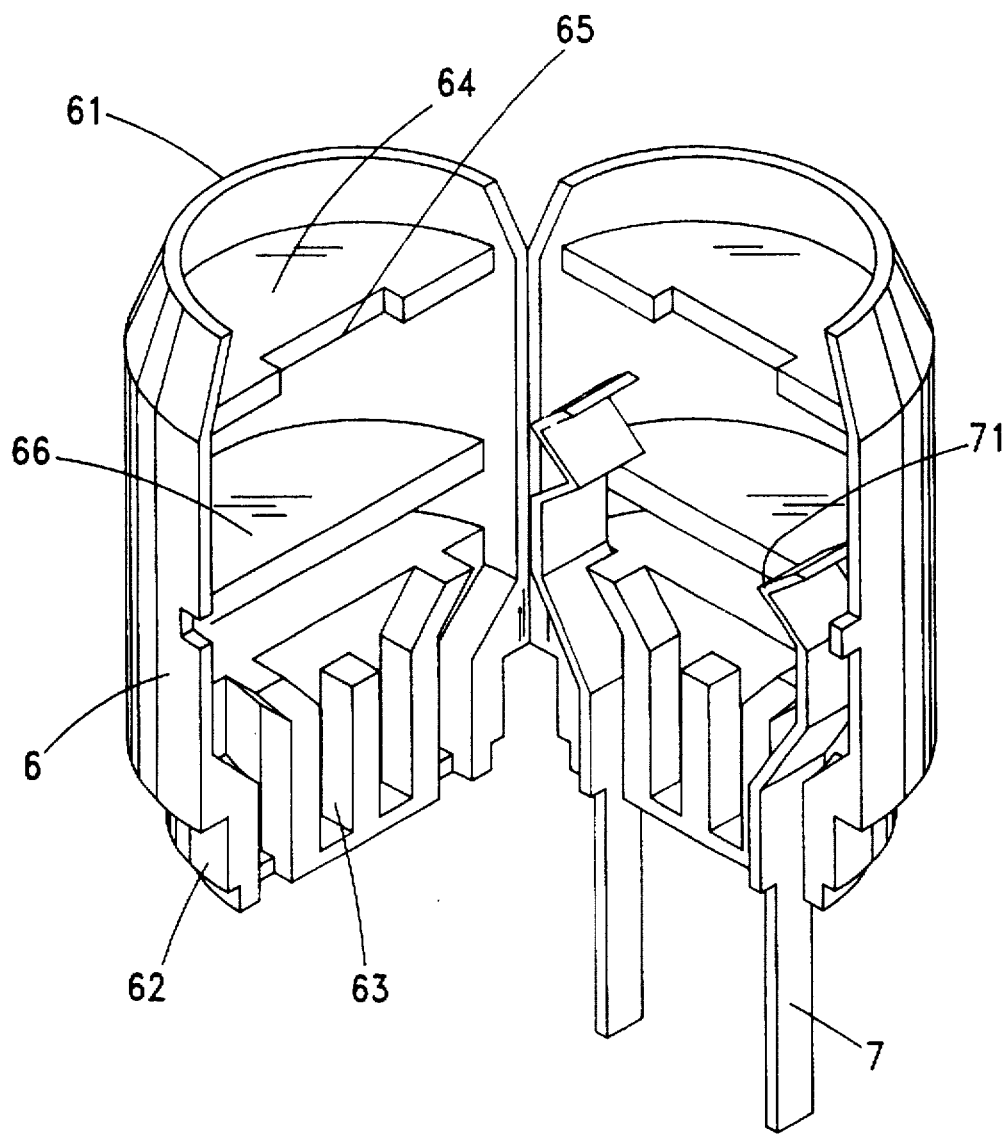
FIG. 2 is a schematic view illustrating the structure of an electrical socket of the present invention.
Figure 3:
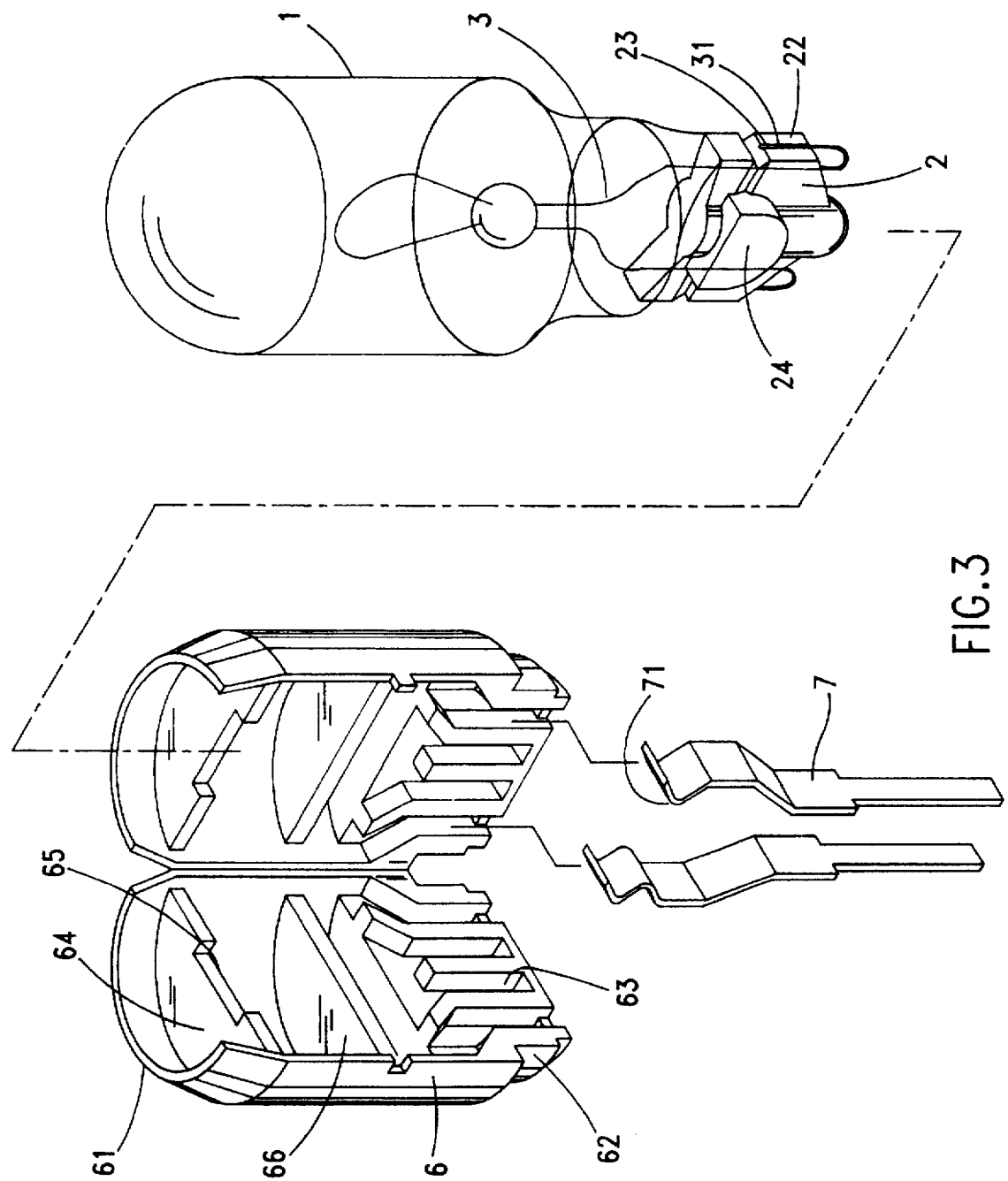
FIG. 3 is a schematic exploded view of the present invention.

With reference to FIGS. 2 and 3, the plug-in type light bulb of the invention essentially comprises a light bulb 1 with a couple of lead wires 3, an electrical socket 6 and, a plurality of electrically conductive plates 7 accommodated in the socket 6. The socket 6 is comprised of two socket halves each of which includes an upper portion 61 and a lower portion 62 joined together. The upper portion 61 has a cover plate 64 disposed at an inner side thereof. The cover plate 64 is provided with a notch 65. A plurality of grooves 63 are provided inside the socket 6 at the lower portion 62 for receiving two conductive plates 7. Each conductive plate 7 has an elastic curved contact terminal 71 at its upper end.

The light bulb 1 is provided with a plug unit 2 at its bottom. The plug unit 2 has two side walls respectively provided with an integrally formed block 24 and two lateral walls 22 against the respective surfaces thereof the contact terminals 31 of the lead wires rest. The lateral walls 22 are each provided with a half round groove 23 across which the corresponding contact terminals 31 are longitudinally inserted with half round therein.

Figure 4:
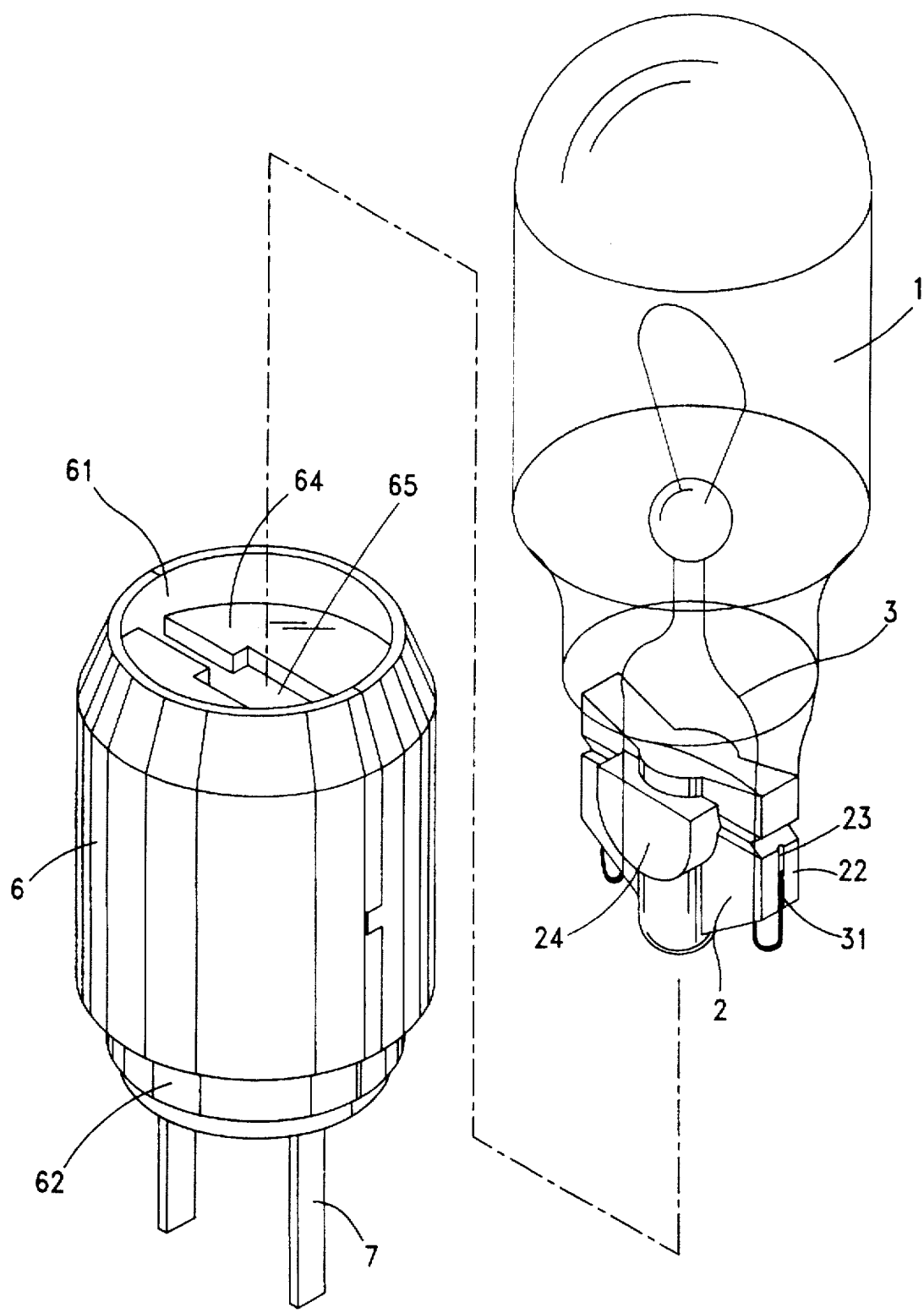
FIG. 4 is a schematic assembled view of the present invention.
Figure 5:
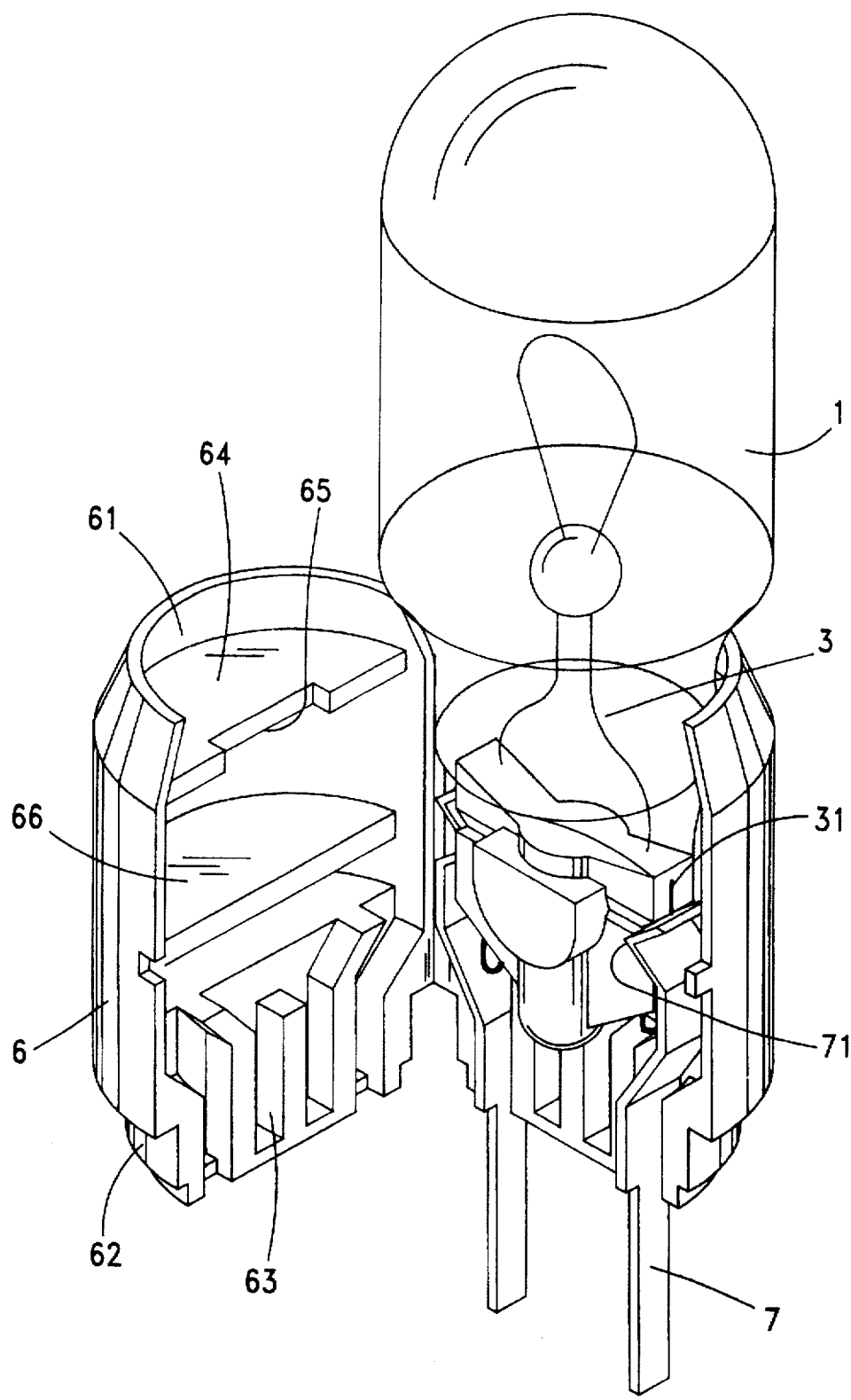
FIG. 5 is a partially exploded view of the internal structure of the present invention.
Figure 6:
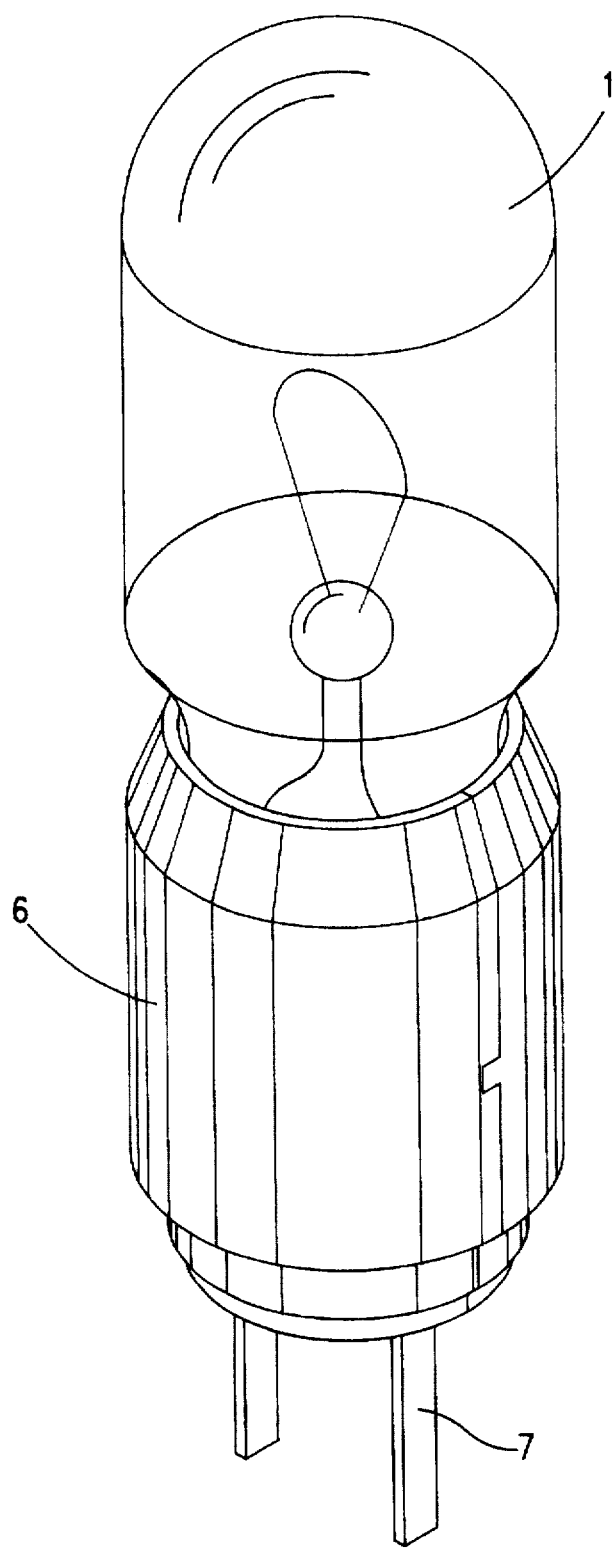
FIG. 6 is a schematic assembled view of the outlook of the present invention.

With reference to FIGS. 3 and 4, after the two socket halves are coupled, the conductive plates 7 are accommodated in the grooves 63 of the lower portion 62, while the cover plates 64 of the socket halves together define a slot due to the arrangement of their respective notches 65 for receiving the plug unit 2. When the plug unit 2 is inserted into the slot, the blocks 24 at the side walls each contact a side wall of an inner cover plate 66 and are secured in position. At the same time, the contact terminals 31 of the lead wires 3 at the lateral walls 22 may just contact the corresponding contact terminals 71 of the conductive plates 7 such that the curved contact terminals 71 may insert into the insert grooves 23 to a suitable extent so that a part of each contact terminal 31 also fits into the corresponding half round groove 23, thus achieving a firm contact between the contact terminals 71 of the conductive plates 7 and the lead wires 3, as shown in FIG. 5.

As mentioned above, the contact terminals 31 of the lead wires 3 are disposed at the two lateral walls of the plug unit 2 so that only two conductive plates 7 are needed to achieve electrical connection. The firm contact relationship between the contact terminals 31 of the lead wires 3 and those of the conductive plates also makes very good electrical conductivity.

Although the present invention has been illustrated and described with reference to the preferred embodiment thereof, it should be understood that it is in no way limited to the details of such embodiment but is capable of numerous modifications within the scope of the appended claims.

What is claimed is:

1. An improved plug-in type light bulb and socket assembly, comprising:

a socket formed by two symmetrical halves, each half having (a) an upper portion and a lower portion with a plurality of grooves formed therein, (b) a cover plate having a notch formed therein disposed in said upper portion, and (c) a pair of electrically conductive plates at least partially received in a respective pair of said plurality of grooves, each of said pair of conductive plates having an elastic curved contact terminal formed at an upper end thereof; and, a light bulb having a plug unit formed on a lower end thereof received in said socket, said light bulb having a pair of lead wires respectively terminated to a pair of contact terminals, said plug unit having a pair of opposing side walls extending longitudinally a first predetermined distance, each of said pair of side walls having a raised block integrally formed thereon and dimensioned to be received in said cover plate notch of a respective socket half, said plug unit having a pair of laterally extending end walls spaced one from another by said first predetermined distance, each of said end walls extending laterally a second predetermined distance, said second predetermined distance being less than said first predetermined distance, each of said end walls having a half round groove formed therein for at least partially receiving a respective one of said contact terminals of the plug unit therein for positioning each of said contact terminals of the plug unit for contact with said elastic curved contact terminal of a respective conductive plate of said socket.

* * * * *